United States Patent [19]
Suh

[11] Patent Number: 5,455,274
[45] Date of Patent: Oct. 3, 1995

[54] HYDROXYAMIDINE DERIVATIVES

[75] Inventor: Hongsuk Suh, Cedar Knolls, N.J.

[73] Assignee: Ciba-Geigy Corporation, Ardsley, N.Y.

[21] Appl. No.: 987,856

[22] Filed: Dec. 9, 1992

[51] Int. Cl.⁶ .................. A61K 31/165; C07C 233/65
[52] U.S. Cl. .............. 514/620; 514/330; 514/542; 514/563; 514/825; 514/863; 546/226; 560/35; 562/440; 564/165
[58] Field of Search .................. 514/825, 863, 514/620, 330, 542, 563; 564/165; 560/35; 562/440; 546/226

[56] References Cited

U.S. PATENT DOCUMENTS

| | | | |
|---|---|---|---|
| 4,034,010 | 7/1977 | Hamane et al. | 260/564 |
| 4,324,794 | 4/1982 | Tidwell et al. | 424/273 |
| 4,499,105 | 2/1985 | Panneman | 514/631 |
| 4,717,736 | 1/1988 | Rokach et al. | 514/486 |
| 4,933,347 | 6/1990 | Tidwell et al. | 514/256 |
| 4,963,589 | 10/1990 | Tidwell et al. | 514/636 |
| 5,135,949 | 4/1992 | von der Saal et al. | 514/620 |

FOREIGN PATENT DOCUMENTS

| | | |
|---|---|---|
| 0108592 | 5/1984 | European Pat. Off. . |
| 0150118 | 7/1985 | European Pat. Off. . |
| 9115201 | 10/1991 | WIPO . |
| 9200011 | 1/1992 | WIPO . |
| 9316036 | 8/1993 | WIPO . |

OTHER PUBLICATIONS

J. Med. Chem., vol. 10, 1123 (1967).
J. Med. Chem., vol. 11, 245 (1968).
J. Med. Chem., vol. 12, 112 (1969).
J. Med. Chem., vol. 21, 1132 (1978).
J. Assoc. Off. Anal. Chem., vol. 69, 624 (1986).
J. Med. Chem., vol. 18, 477 (1975).
J. Med. Chem., vol. 16, 970 (1973).
Arch. Pharm. (Weinheim), 325, 61–62 (1992).
J. Pharm. Exp. Ther., vol. 256, No. 3, 883–889 (1991).
Antimicrobial Agents and Chemotherapy, pp. 1678–1684 (1990).
Arzneimittelforschung, 35, 1009 (1985).
Acta Chimica Academiae Scientiarum Hungaricae, Tomus 66(4) pp. 439–445 (1970).

*Primary Examiner*—Peter O'Sullivan
*Attorney, Agent, or Firm*—Norbert Gruenfeld

[57] ABSTRACT

The invention relates to the compounds of the formula

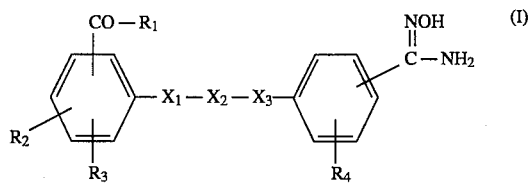

wherein the C(=NOH)-NH$_2$ group may be in tautomeric form, and pharmaceutically acceptable salts thereof, in which:

$R_1$ is amino or amino which is mono- or disubstituted by a substituent selected from an aliphatic hydrocarbon radical, an araliphatic hydrocarbon radical, an aromatic radical, and a cycloaliphatic hydrocarbon radical or is amino which is disubstituted by a divalent aliphatic hydrocarbon radical or a said radical interrupted by oxygen;

$R_2$ is hydrogen, halogen, trifluoromethyl, an aliphatic hydrocarbon radical or hydroxy; or $R_2$ is hydroxy which is etherified by an aliphatic alcohol, araliphatic alcohol, or aromatic alcohol or which is esterified by an aliphatic or araliphatic carboxylic acid; or $R_2$ is hydroxy which is etherified by an aliphatic alcohol which is substituted by carboxy, by esterified carboxy or by amidated carboxy;

$X_1$ and $X_3$, independently of one another, are oxygen (—O—) or sulphur (—S—); and $X_2$ is a divalent aliphatic hydrocarbon radical which may be interrupted by an aromatic radical; and $R_3$ and $R_4$, independently of one another, are hydrogen, halogen, trifluoromethyl, an aliphatic hydrocarbon radical, hydroxy or hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein a cycloaliphatic hydrocarbon radical may be substituted by an aliphatic radical.

The compounds are useful as selective LTB$_4$ receptor antagonists in the treatment of conditions or syndromes in mammals which are responsive to LTB$_4$ receptor antagonism.

17 Claims, No Drawings

HYDROXYAMIDINE DERIVATIVES

SUMMARY OF THE INVENTION

The invention relates to the hydroxyamidinophenoxyalkoxyphenyl derivatives and thio analogs as defined herein which are particularly useful as selective leukotriene $B_4$ ($LTB_4$) receptor antagonists, methods for preparation thereof, pharmaceutical compositions comprising said compounds, and a method of antagonizing $LTB_{,4}$ and of treating conditions or syndromes in mammals which are responsive to $LTB_4$ antagonism using said compounds or pharmaceutical compositions comprising said compounds of the invention.

Leukotriene $B_4$ ($LTB_4$) is an important inflammatory mediator being a potent chemotactic agent and activator of polymorphonuclear leucocytes (PMN's) and monocytes. It modulates the production and effects of other important inflammatory mediators e.g. interleukin-1 and gamma interferon. $LTB_4$ has been implicated in the pathogenesis of a number of inflammatory diseases, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma.

The compounds of the invention are useful for the treatment of the conditions mediated by $LTB_4$ which are cited above. In addition, the compounds are also useful for the treatment of pain and osteoarthritis, for the treatment of ocular conditions, such as ocular allergy and inflammation, and also for the treatment of dermatitis, such as atopic and contact dermatitis.

DETAILED DESCRIPTION OF THE INVENTION

The invention relates to hydroxyamidinophenoxyalkoxyphenyl derivatives and thio analogs of the formula

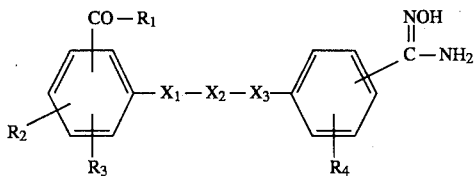
(I)

wherein the C(=NOH)—$NH_2$ group may be in tautomeric form; and pharmaceutically acceptable salts thereof, in which:

$R_1$ is amino or amino which is mono- or disubstituted by a substituent selected from an aliphatic hydrocarbon radical, an araliphatic hydrocarbon radical, an aromatic radical, and a cycloaliphatic hydrocarbon radical, or is amino which is disubstituted by a divalent aliphatic hydrocarbon radical or a said radical interrupted by oxygen;

$R_2$ is hydrogen, halogen, trifluoromethyl, an aliphatic hydrocarbon radical, or hydroxy; or $R_2$ is hydroxy which is etherified by an aliphatic alcohol, araliphatic alcohol or aromatic alcohol, or which is esterified by an aliphatic or araliphatic carboxylic acid; or $R_2$ is hydroxy which is etherified by an aliphatic alcohol which is substituted by carboxy, by esterified carboxy or by amidated carboxy;

$X_1$ and $X_3$, independently of one another, are oxygen (—O—) or sulphur (—S—); and $X_2$ is a divalent aliphatic hydrocarbon radical which may be interrupted by an aromatic radical;

$R_3$ and $R_4$ are, independently of one another, hydrogen, halogen, trifluoromethyl, an aliphatic hydrocarbon radical, hydroxy or hydroxy which is etherified by an aliphatic alcohol or which is esterified by an aliphatic or araliphatic carboxylic acid; and wherein aryl in the above definitions may be, independently of one another, further substituted by one or more substituents selected from halogen, trifluoromethyl, an aliphatic hydrocarbon radical, hydroxy, or hydroxy which is etherified by an aliphatic alcohol or which is esterified by an aliphatic or araliphatic carboxylic acid;

wherein a cycloaliphatic hydrocarbon radical may be substituted by an aliphatic radical;

which are particularly useful as selective $LTB_4$ antagonists, methods for preparation thereof, pharmaceutical compositions comprising said compounds, and a method of antagonizing $LTB_4$ and of treating diseases in mammals which are responsive to $LTB_4$ antagonism using said compounds or pharmaceutical compositions comprising said compounds of the invention.

The compounds of the invention wherein the C(=NOH)—$NH_2$ group is in tautomeric form are represented by formula I'

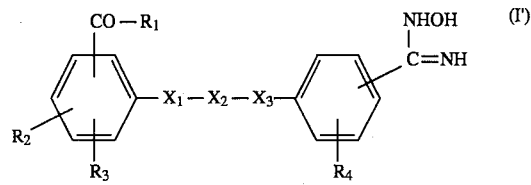
(I')

wherein $R_1$, $R_2$, $R_3$, $R_4$, $X_1$, $X_2$ and $X_3$ have meaning as defined for formula I.

Compounds according to the invention can form acid addition salts, especially pharmaceutically acceptable salts. These are formed, for example, with inorganic acids, such as mineral acids, for example sulfuric acid, a phosphoric or hydrohalic acid, or with organic sulfonic acids, such as ($C_1$–$C_4$—) alkane- or arylsulfonic acids which are unsubstituted or substituted, for example, by halogen, for example methane- or toluenesulfonic acid. Preferred are salts formed with hydrochloric acid and methanesulfonic acid.

The general definitions used below have, if not defined differently, the following meanings:

An aliphatic hydrocarbon radical is, for example, lower alkyl, lower alkenyl and secondarily lower alkynyl.

An araliphatic hydrocarbon radical is, for example, optionally substituted phenyl-lower alkyl and secondarily phenyl-lower alkenyl and phenyl-lower alkynyl.

A cycloaliphatic hydrocarbon radical is, for example, cycloalkyl and secondarily cycloalkenyl, which is unsubstituted or mono- or polysubstituted, for example, disubstituted, by lower alkyl.

A divalent aliphatic hydrocarbon radical is, for example, lower alkylene.

A divalent aliphatic radical interrupted by oxygen is, for example, lower alkylene interrupted by oxygen, e.g. ethylene-O-ethylene.

A divalent aliphatic hydrocarbon radical which is interrupted by an aromatic radical is, for example, lower alkylene-phenylene-lower alkylene or lower alkylene-naphthylene-lower alkylene.

An aliphatic alcohol is, for example, a lower alkanol or lower alkenol, and an araliphatic alcohol is, for example, a phenyl-lower alkanol.

An aromatic alcohol is, for example, a phenol which is unsubstituted or is further substituted such as monosubstituted, for example, disubstituted or secondarily trisubstituted.

Hydroxy which is etherified by an aliphatic or araliphatic alcohol is, for example, lower alkoxy or lower alkenyloxy and phenyl-lower alkoxy.

An aliphatic carboxylic acid is, for example, a lower alkanoic or lower alkenoic acid, and an araliphatic carboxylic acid is, for example, a phenyl-lower alkanoic acid.

Hydroxy which is esterified by an aliphatic or araliphatic carboxylic acid is, for example, lower alkanoyloxy, secondarily lower alkenoyloxy, or is phenyl-lower alkanoyloxy.

An acyl radical which is derived from an an organic carboxylic acid is, for example, lower alkanoyl, phenyl-lower alkanoyl or unsubstituted or substituted aroyl, such as benzoyl, naphthoyl, indanoyl or fluorenoyl, or heteroaroyl such as pyfidylcarbonyl, thienylcarbonyl, pyrrolylcarbonyl, furanylcarbonyl, and imidazolylcarbonyl.

An acyl radical which is derived from an organic carbonic acid is, for example, alkoxycarbonyl or alkenyloxycarbonyl which in each case are unsubstituted or substituted by an aromatic radical or is cycloalkoxycarbonyl which unsubstituted or substituted by lower alkyl.

An acyl radical which is derived from a sulfonic acid is, for example, alkanesulfonyl, arylalkanesulfonyl, cycloalkanesulfonyl or arylsulfonyl.

An acyl radical which is derived from a carbamic acid is, for example, amino-carbonyl which is substituted by alkyl, arylalkyl or aryl.

An aromatic radical is, for example, unsubstituted or substituted such as monosubstituted or polysubstituted, for example, disubstituted or secondarily trisubstituted carbocyclic aryl, such as phenyl, naphthyl, indanyl or fluorenyl, or heterocyclic aryl, such as pyridyl, thienyl, pyrrolyl, furanyl, and imidazolyl.

Aryl represents preferably monocarbocyclic aryl, advantageously optionally substituted phenyl, such being phenyl or phenyl substituted by e.g. lower alkyl, lower alkoxy, halogen or trifluoromethyl.

The aromatic radicals referred to before and hereafter are generally unsubstituted or further substituted such as monosubstituted or polysubstituted, for example disubstituted or secondarily trisubstituted, in particular, for example, by a substituent selected from the group consisiting of halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy, and phenyl-lower alkanoyloxy.

Preferred positions of the following structural elements in the corresponding phenyl ring in formula I are: positions 4 (para) or 5 (meta) for —CO—$R_1$, position 2 (ortho) or 3 (meta) for $R_2$, and position 4 (para) for —C(=NOH)—$NH_2$.

The term "substituted by one or more substituents" refers preferably to one, two or three such substituents, advantageously one or two.

The expression "lower" means that corresponding groups and compounds in each case contain in particular not more than 7, preferably not more than 4, carbon atoms.

Halogen is, in particular, fluorine, chlorine or bromine, and furthermore includes iodine.

Lower alkyl is, in particular, $C_1$–$C_7$-alkyl and is, for example, methyl, ethyl, n-propyl, isopropyl, n-butyl, isobutyl, sec-butyl, tert-butyl and furthermore includes corresponding pentyl, hexyl and heptyl radicals. $C_1$–$C_4$-Alkyl is preferred.

Lower alkenyl is, in particular, $C_3$–$C_7$-alkenyl and is, for example, 2-propenyl or 1-, 2- or 3-butenyl. $C_3$–$C_5$-Alkenyl is preferred.

Lower alkynyl is, in particular, $C_3$–$C_7$-alkynyl and is preferably propargyl.

Phenyl-lower alkyl is, in particular, phenyl-$C_1$–$C_4$-alkyl and is preferably benzyl, 1- and 2-phenethyl, while phenyl-lower alkenyl and phenyl-lower alkynyl are, in particular, phenyl-$C_2$–$C_5$-alkenyl and -alkynyl, in particular 2-phenylvinyl, 3-phenylallyl and 3-phenylpropargyl.

Cycloalkyl is, in particular, $C_3$–$C_7$-cycloalkyl and is, for example, cyclopropyl, cyclobutyl, cyclopentyl, cyclohexyl and cycloheptyl. Cyclopentyl and cyclohexyl are preferred.

Cycloalkenyl is, in particular, $C_3$–$C_7$-cycloalkenyl and is preferably cyclopent-2- or -3-enyl, or cyclohex-2- and -3-en-yl.

Lower alkylene e.g. in amino which is disubstituted by lower alkylene is, in particular, $C_2$–$C_6$-alkylene and is, for example, butylene, pentylene, or 2,6-butylene. Preferred is $C_4$–$C_5$-alkylene, especially pentylene.

Lower alkylene $X_2$ is, in particular, $C_2$–$C_8$-alkylene, preferably straight-chain, and is, for example, ethylene, propylene, butylene, pentylene, hexylene, heptylene and also octylene. $C_4$–$C_7$-Alkylene is preferred, especially pentylene and also butylene, hexylene or heptylene.

Lower alkylene which is interrupted by a phenyl radical ($X_2$) is, in particular, lower alkylene-phenylene-lower alkylene or lower alkylene-naphthylene-lower alkylene such as $C_2$–$C_4$-alkylene-phenylene-$C_2$–$C_4$-alkylene or $C_2$–$C_4$-alkylene-naphthylene -$C_2$–$C_4$-alkylene, preferably straight-chain, and is, for example, methylene-phenylene-methylene, 1,2-ethylene-phenylene-1,2-ethylene, such as 1,2-ethylene-1,4-phenylene-1,2-ethylene, 1,3-propylene-phenylene-1,3-propylene, such as 1,3-propylene-1,4-phenylene-1,3-propylene, or butylene-phenylene-butylene radicals, also a corresponding 1,2-ethylene-naphthylene-1,2-ethylene radical. $C_2$–$C_4$-alkylene-phenylene-$C_2$–$C_4$-alkylene or $C_2$–$C_3$-alkylene -naphthylene-$C_2$–$C_3$-alkylene is preferred, especially 1,2-ethylene-1,4-phenylene-1,2-ethylene.

Lower alkoxy is, in particular, $C_1$–$C_7$-alkoxy and is, for example, methoxy, ethoxy, n-propyloxy, isopropyloxy, n-butyloxy, isobutyloxy, sec-butyloxy, tert-butyloxy and furthermore includes corresponding pentyloxy, hexyloxy and heptyloxy radicals. $C_1$–$C_4$-Alkoxy is preferred.

Lower alkenyloxy is, in particular, $C_3$–$C_7$-alkenyloxy and is, for example, allyloxy or but-2-en- or but-3-enyloxy. $C_3$–$C_5$-Alkenyloxy is preferred.

Phenyl-lower alkoxy is, in particular, phenyl-$C_1$–$C_4$-alkoxy, such as benzyloxy, 1- or 2-phenylethoxy, or 1-, 2- or 3-phenylpropyloxy.

Lower alkanoyloxy is, in particular, $C_2$–$C_8$-alkanoyloxy, in particular, $C_2$–$C_5$-alkanoyloxy, such as acetyloxy, propionyloxy or pivaloyoxy.

Lower alkenoyloxy is, in particular, $C_3$–$C_8$-alkenoyloxy, in particular, $C_3$–$C_5$-alkenoyloxy, such as propenoyloxy.

Phenyl-lower alkanoyloxy is, in particular, phenyl-$C_2$–$C_8$-alkanoyloxy, in particular, phenyl-$C_2$–$C_5$alkanoyloxy, such as phenylacetyloxy, phenylpropionyloxy or phenylpivaloyloxy.

Alkoxycarbonyl is, in particular, $C_2$–$C_{12}$-alkoxycarbonyl and is, for example, methoxy-, ethoxy-, propyloxy- pivaloyloxy- or octyloxy-carbonyl. $C_2$–$C_9$-Alkoxycarbonyl is preferred.

Alkenyloxycarbonyl is, in particular, $C_3$–$C_{12}$-alkenyloxycarbonyl, for example, allyloxycarbonyl. Preferred is $C_3$–$C_5$-alkenyloxycarbonyl.

Cycloalkyloxycarbonyl is, in particular, $C_3$–$C_7$-cycloalkoxycarbonyl, preferred is cyclopentyloxycarbonyl or cyclohexyloxycarbonyl.

Alkanesulfonyl is, in particular, $C_1$–$C_7$-alkanesulfonyl and is, for example, methane-, ethane-, n-propane- or isopropanesulfonyl. $C_1$–$C_4$-Alkanesulfonyl is preferred.

Arylalkanesulfonyl is, in particular, phenyl-$C_1$-$C_7$-alkanesulfonyl, for example, benzyl- or 1- or 2-phenylethanesulfonyl. Phenyl-$C_1$-$C_4$-alkane-sulfonyl is preferred.

Cycloalkanesulfonyl is, in particular, $C_3$-$C_7$-cycloalkanesulfonyl, preferred is cyclopentanesulfonyl or cyclohexanesulfonyl.

Naphthyl is 1- or 2-naphthyl.

Indanyl is, for example, 1-, 2-, 3- or 4-indanyl.

Fluorenyl is, for example, 1-, 2-, 3-, 4- or 5-fluorenyl.

Lower alkanoyl is, in particular, $C_1$-$C_7$-alkanoyl and is, for example, formyl, acetyl, propionyl, butyryl, isobutyryl or pivaloyl. $C_2$-$C_5$-Alkanoyl is preferred.

Phenyl-lower alkanoyl is, in particular, phenyl-$C_2$-$C_7$-alkanoyl and is, for example, phenylacetyl or 2- or 3-phenylpropionyl. Phenyl-$C_2$-$C_4$-alkanoyl is preferred.

Substituted aroyl represents aroyl, such as benzoyl, which is substituted e.g. by lower alkoxy, lower alkyl, hydroxy, hydroxymethyl or by acyloxymethyl (such as lower alkanoyloxymethyl or benzoyloxymethyl.

Naphthoyl is 1- or 2-naphthoyl.

Indanoyl is, for example, 1-, 2-, 3- or 4-indanoyl.

Fluorenoyl is, for example, 1-, 2-, 3-, 4- or 5-fluorenoyl.

Esterified carboxyl represents preferably lower alkoxycarbonyl or aryl-lower alkoxycarbonyl.

Amidated carboxyl represents preferably aminocarbonyl, hydroxyaminocarbonyl, mono- or di-lower alkylaminocarbonyl, (mono-aryl-mono-lower alkyl)aminocarbonyl, mono- or di-(aryl-lower alkyl)aminocarbonyl or (mono-aryl-lower alkyl-mono-lower alkyl)aminocarbonyl.

The compounds of the invention exhibit valuable pharmacological properties in mammals, and are particularly useful as selective Leukotriene $B_4$ ($LTB_4$) receptor antagonists, e.g. for the treatment of a condition or syndrome in a mammal responsive to the selective antagonism of $LTB_4$ receptors, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma. The compounds of the invention are also useful as analgesics for the treatment of pain of any origin, and for the treatment of osteoarthritis, also for the treatment of ocular conditions, such as ocular allergy and inflammation, and also for the treatment of dermatitis, e.g. atopic and contact dermatitis.

The above-cited properties are demonstrable in in vitro and in vivo tests, using advantageously mammals, e.g. rats. Said compounds can be applied in vitro in the form of solutions, e.g. preferably aqueous solutions, and in vivo either enterally or parenterally, advantageously orally, e.g. as a suspension or in aqueous solution. The dosage in vitro may range between about 0.5 ng/ml and about 100 ng/ml. The dosage in vivo may range, depending on the route of administration, between about 1 and about 1000 mg/kg per day.

Beneficial effects are evaluated in pharmacological tests generally known in the art, e.g. as illustrated herein.

Receptor Binding with [$^3$H]-$LTB_4$ to Intact Human Neutrophils:

Neutrophils (PMN's) are prepared from uncoagulated human venous blood. Blood is dispersed into 50 ml polypropylene tubes containing 15 ml of HESPAN (Dupont, Wilmington, Del.), and mixed. Tubes are allowed to stand at room temperature for 40 minutes until most of the red blood cells sediment. The supernatants are removed and centrifuged for 5–10 min at 400×g. The remaining pellets are diluted in 70 ml of Phosphate Buffered Saline without calcium and magnesium (PBS without metals; GIBCO, Grand Island, N.Y.) and 35 ml of this suspension are placed in each of two polypropylene tubes containing 15 ml of Ficoll-Paque (Sigma, St. Louis, Mo.). Gradients are then centrifuged for 15 minutes at 420× g. The mononuclear cell layer is discarded and the remaining red blood cell pellet is resuspended in 10 ml of PBS without metals. Twenty ml of filtered deionized water are added to the suspension for approximately 20 sec followed by the same volume of buffer at two times the normal concentration. The cell suspension is mixed and centrifuged for 5 rain at 200×g, followed by one wash with buffer, and final resuspension.

Binding of [$^3$H]$LTB_4$ to $LTB_4$ receptors is measured in intact human polymorphonuclear leukocytes, as described by Gorman and Lin (Gorman, R. and Lin, A Methods Enzymol. 141: 372–378, 1987). Intact human neutrophils are suspended in Hank's Balanced Salt Solution (HBSS) at a concentration of 3×10$^6$ cells/assay tube. An aliquot of the cell suspension (300 μl) is added to triplicate tubes containing 50 μl[3H]$LTB_4$ (specific activity 32 Ci/mmol, DuPont-NEN, Boston, Mass.) at a final concentration of 0.5 nM, 100 μl buffer and 50 μl drug or buffer. Nonspecific binding is determined in the presence of 300 nM $LTB_4$. The reaction is initiated by addition of cell suspension and continued at 0° C. for 20 min. Bound radioactivity is isolated by vacuum filtration through Whatman GF/C glass fiber filters using a Brandel cell harvester and unbound radioactivity removed with 2×5 ml washes with ice-cold saline. Filters are placed in polyethylene scintillation mini-vials to which is added 3.5 ml of Formula-989 scintillation cocktail (NEN). After equilibration, radioactivity determinations and data calculations are performed using non-linear regression analysis on RS/1.

$LTB_4$-Induced PMN Aggregation

Human PMNs are prepared as previously described. Neutrophil aggregation is assessed by monitoring the intensity of light passing through a suspension of cells (Craddock et al., J. Clin. Invest. 60: 260–264, 1977) using a Payton dual channel aggregometer (model 300BD). Cuvettes containing 0.25 ml of cell suspension (25×10$^6$ cells/ml) in PBS without calcium and magnesium are incubated with 5 μg/ml ml of cytochalasin B for 2 minutes at 37° C. 5 μl of 2 μM $LTB_4$ in PBS (20 nM final concentration) are added and the aggregation response monitored for 3–5 min, the time required for optimal response, Compounds are solubilized in 0.01M DMSO and then diluted in PBS to 0.001 M. 5 μl of compound solution is added along with cytochalasin B and cells as described above. Following the preincubation period 5 μl of 2 μM $LTB_4$ are added and aggregation is measured. Percent inhibition of aggregation is calculated by comparing peak heights in the presence and absence of compound. Percent inhibition is plotted as a function of the log concentration of compound and the $IC_{50}$ determined directly from the graph.

$LTB_4$-Induced Neutropenia in the Rat

Male Sprague Dawley rats (crl: CDBR; Charles River, Wilmington, Mass.) (250–300 grams) are fasted overnight prior to the experiment. At least six animals are used per treatment group. Rats are given vehicle or compound either intravenously or orally and at intervals after dosing, neutrophil counts are determined from blood samples obtained just prior to and 20 seconds after intravenous infusion of 200 ng $LTB_4$. In studies where compound is administered orally, drug is given by gavage. When drug is administered intravenously, rats are first anesthetized with 50 mg/kg i.p. of Sodium Pentabarbital. The jugular vein is exposed and cleaned of the surrounding tissue. At 3, 4 or 18 hours following administration of compound or vehicle by either route, blood samples are taken (0.3 ml of blood in 1.5 ml polypropylene microcentrifuge tube containing 0.01 mi 7.5% EDTA). Blood neutrophil counts are determined using a Technicon H-1 hematology instrument. Antagonism of the $LTB_4$-induced neutropenia response for the compounds tested is calculated.

Illustrative of the invention, the compound of example 1,4-[5-[4-[amino(hydroxyimino)methyl] phenoxy]pentyloxy]-2-hydroxy-N,N-bis(1-methylethyl)benzamide inhibits $LTB_4$-induced PMN aggregation at an $IC_{50}$ of about 10 nM in vitro. Said compound also causes inhibition of $LTB_4$-induced neutropenia in the rat when administered at a dose of about 0.5 mg./Kg p.o., as determined at four hours after administration.

Analgesic activity can be demonstrated e.g. in the Randall-Selino test for analgesia, e.g. as described in Arch. Int. Pharmacodyn. Ther. 111, 409 (1957).

Bronchial effects such as anti-asthmatic activity, can be demonstrated in the antigen-induced guinea pig bronchoconstriction test, e.g. as described by Anderson et al, Br. J. Pharmacol. 1983, 78, 67–74.

The trinitrobenzenesulfonic acid-induced chronic colitis test in the rat, e.g. as described by Wallace et al, Gastroenterology 1989, 96, 29–36, can be used to evaluate compounds for effects indicative of utility in inflammatory bowel diseases.

The arachidonic acid-induced mouse ear edema test, e.g. as described by Young et al, J. Invest, Dermatol. 1984, 82,367–371 can be used to evaluate compounds for antiinflammatory activity and for effects indicative of utility in dermatological disorders such as psoriasis.

The invention especially relates to compounds of formula I and pharmaceutically acceptable salts thereof, in which:

$R_1$ is amino or amino which is mono- or disubstituted by a substituent selected from lower alkyl, lower alkenyl, lower alkynyl, phenyl-lower alkyl, phenyl-lower alkenyl, phenyl-lower alkynyl, phenyl, naphthyl, indanyl, fluorenyl, cycloalkyl, and cycloalkenyl, cycloalkyl and cycloalkenyl each being unsubstituted or mono- or polysubstituted by lower alkyl, or is amino which is disubstituted by lower alkylene;

$R_2$ is hydrogen, halogen, trifluoromethyl, lower alkyl, lower alkenyl, lower alkynyl, hydroxy, lower alkoxy, lower alkenyloxy, phenyl-lower alkoxy, phenoxy, lower alkanoyloxy, lower alkenoyloxy or phenyl-lower alkanoyloxy; or $R_2$ is lower alkoxy substituted by carboxy, lower alkoxycarbonyl, aminocarbonyl or mono- or di-lower alkylaminocarbonyl;

$X_1$ and $X_3$, independently of one another are O or S;

$X_2$ is lower alkylene, lower alkylene-phenylene-lower alkylene or lower alkylene-naphthylene-lower alkylene; and $R_3$ and $R_4$ are independently of one another, hydrogen, halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy or phenyl-lower alkanoyloxy;

wherein the aromatic radicals in the above definitions may be independently of one another, substituted by one or more substituents selected from halogen, trifluoromethyl, lower alkyl lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy.

The invention especially relates to compounds of formula I and pharmaceutically acceptable salts thereof, in which:

$R_1$ is amino which is mono- or disubstituted by a substituent selected from $C_1$–$C_7$-alkyl, phenyl-$C_1$–$C_7$-alkyl, phenyl and $C_3$–$C_6$-cycloalkyl, $C_3$–$C_6$-cycloalkyl being unsubstituted or mono- or polysubstituted by $C_1$–$C_7$-alkyl, or is amino which is disubstituted by $C_3$–$C_6$-alkylene;

$R_2$ is hydrogen, $C_1$–$C_7$alkoxy, phenyl-$C_1$–$C_4$-alkoxy or hydroxy; or $R_2$ is $C_1$–$C_7$-alkoxy substituted by aminocarbonyl or lower alkoxycarbonyl;

$X_1$ and $X_3$ each are —O—, or furthermore are, independently of one another, —O— or —S—;

$R_3$ and $R_4$ are, independently of one another, hydrogen, halogen, trifluoromethyl, $C_1$–$C_7$-alkyl, or $C_1$–$C_7$-alkoxy;

wherein phenyl in the above definitions is unsubstituted or, furthermore, independently of one another, substituted by one or more substituents selected from halogen, trifluoromethyl, $C_1$–$C_7$-alkyl, and $C_1$–$C_7$-alkoxy.

The invention especially relates to compounds of formula I and pharmaceutically acceptable salts thereof, in which —CO—$R_1$ is located in position 4 (para) or 3 or 5 (meta) of the corresponding phenyl ring with respect to —$X_1$—; $R_2$— is located in position 2 (ortho) or 3 (meta) of the corresponding phenyl ring with respect to —$X_1$—; and —C(=NOH)—$H_2$ is located in position 4 (para) of the corresponding phenyl ring with respect to —$X_3$—.

The invention especially relates to compounds of formula IA

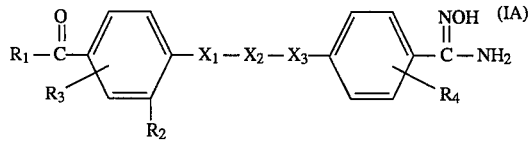

wherein the C(=NOH)—$NH_2$ group may be in tautomeric form, and pharmaceutically acceptable salts thereof, in which:

$R_1$ is di-$C_1$–$C_4$-alkylamino, such as di-ethylamino or di-isopropylamino, $C_1$–$C_4$alkyl-phenylamino, such as phenyl-isopropyl-amino, $C_1$–$C_4$alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino which is unsubstituted or substituted by $C_1$–$C_4$-alkyl, such as 2-methyl- 1-piperidino;

$R_2$ is hydrogen, hydroxy, halogen or $C_1$–$C_4$-alkoxy, such as methoxy; or $R_2$ is $C_1$–$C_4$-alkoxy which is substituted by carboxy, lower alkoxycarbonyl, aminocarbonyl, hydroxyaminocarbonyl, or by mono- or di-lower alkylaminocarbonyl; $X_1$ and $X_3$ are —O—;

$X_2$ is $C_4$–$C_7$-alkylene, such as pentylene; and $R_3$ and $R_4$ are hydrogen, halogen, trifluoromethyl, $C_1$–$C_4$-alkyl, or $C_1$–$C_4$-alkoxy.

The invention especially relates to compounds of formula IA and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as di-cyclohexylamino which is unsubstituted or substituted by $C_1$–$C_4$-alkyl, or 1-piperidino substituted by $C_1$–$C_4$-alkyl, such as 2-methyl-1-piperidino;

$R_2$ is hydrogen, hydroxy, or $C_1$–$C_4$-alkoxy, such as methoxy; or $R_2$ is $C_1$–$C_4$-alkoxy substituted by $C_1$–$C_4$-alkoxycarbonyl, such as ethoxycarbonylmethyl, or by aminocarbonyl;

$X_1$ and $X_3$ are —O—;

$X_2$ is $C_4$–$C_7$-alkylene, such as pentylene; and $R_3$ and $R_4$ are hydrogen.

The invention further especially relates to compounds of formula IA and pharmaceutically acceptable salts thereof, in which:

$R_1$ is di-$C_1$–$C_4$-alkylamino, such as di-ethylamino or di-isopropylamino, or $C_1$–$C_4$-alkyl(phenyl)amino such as phenyl-isopropyl-amino;

$R_2$ is hydrogen or $C_1$–$C_4$-alkoxy, such as methoxy;

$X_1$ and $X_3$ are —O—;

$X_2$ is $C_4$–$C_7$alkylene, especially pentylene; and $R_3$ and $R_4$ are hydrogen.

The invention further especially relates to compounds of formula IA and pharmaceutically acceptable salts thereof, in which:

$R_1$ is di-$C_1$–$C_4$-alkylamino, such as di-isopropylamino;

$R_2$ is hydrogen or $C_1$–$C_4$-alkoxy, such as methoxy;

$X_1$ and $X_3$ are —O—;

$X_2$ is $C_4$–$C_7$-alkylene, especially pentylene; and $R_3$ and $R_4$ are hydrogen.

The invention also particularly relates to the compounds of formula IB

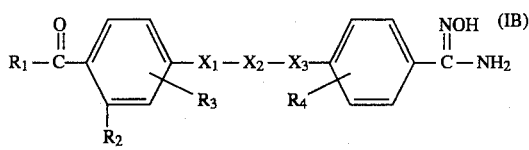

wherein the C(=NOH)—$NH_2$ group may be in tautomeric form, and pharmaceutically acceptable salts thereof, in which:

$R_1$ is di-$C_1$–$C_4$-alkylamino, such as di-ethylamino or di-isopropylamino, $C_1$–$C_4$alkyl-(phenyl)amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydrogen, hydroxy, halogen or $C_1$–$C_4$-alkoxy, such as methoxy; or $R_2$ is $C_1$–$C_4$-alkoxy which is substituted by carboxy, lower alkoxycarbonyl, aminocarbonyl, hydroxyaminocarbonyl or by mono- or di-lower alkylaminocarbonyl;

$X_1$ and $X_3$ are —O—;

$X_2$ is $C_4$–$C_7$-alkylene, such as pentylene; and $R_3$ and $R_4$ are independently of one another hydrogen, halogen, trifluoromethyl, $C_1$–$C_4$-alkyl, or $C_1$–$C_4$-alkoxy.

The invention especially relates to compounds of formula IB and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino which is unsubstituted or substituted by $C_1$–$C_4$-alkyl, such as 2-methyl-1-piperidino;

$R_2$ is hydrogen, fluoro, chloro, hydroxy or $C_1$–$C_4$-alkoxy, such as methoxy; or $R_2$ is $C_1$–$C_4$-alkoxy substituted by carboxy, $C_1$–$C_4$-alkoxycarbonyl, such as ethoxycarbonylmethoxy, or by aminocarbonyl, such as carbamoylmethoxy;

X1 and $X_3$ are —O—;

$X_2$ is $C_4$–$C_7$-alkylene, such as pentylene; and $R_3$ and $R_4$ are hydrogen.

The invention further especially relates to compounds of formula IB and pharmaceutically acceptable salts thereof, in which:

$R_1$ is di-$C_1$–$C_4$-alkylamino, such as di-ethylamino or di-isopropylamino, or $C_1$–$C_4$-alkyl(phenyl)amino such as phenyl-isopropyl-amino;

$R_2$ is hydrogen, fluoro, chloro, hydroxy or $C_1$–$C_4$-alkoxy, such as methoxy; or $R_2$ is carboxy-$C_1$–$C_4$-alkoxy, $C_1$–$C_4$-alkoxycarbonyl-$C_1$–$C_4$-alkoxy, such as ethoxycarbonylmethoxy, or carbamoyl-$C_1$–$C_4$-alkoxy, such as carbamoylmethoxy;

$X_1$ and $X_3$ are —O—;

$X_2$ is $C_4$–$C_7$-alkylene, especially pentylene; and $R_3$ and $R_4$ are hydrogen.

When $R_2$ in the above compounds of formula IA and IB is substituted $C_1$–$C_4$-alkoxy, preferred are such compounds in which the ether oxygen and the substituent are separated by one carbon atom.

The invention further relates to methods for the preparation of the compounds according to the invention. The preparation of compounds of the formula I is, for example, characterized in that, a compound of the formula II

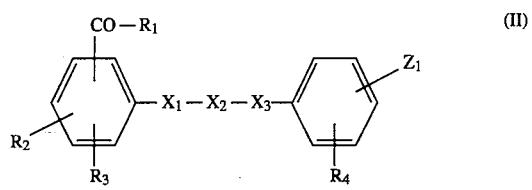

or a salt thereof in which $Z_1$ is a radical which can be convened into the grouping —C(=NOH)—$NH_2$, is treated with hydroxylamine or a salt thereof, optionally in hydroxy-protected form, and, if desired, a compound of the formula I or a salt thereof obtainable according to the process or in another manner is converted into another compound or a salt thereof according to the invention, a free compound of the formula I obtainable according to the process is convened into a salt, a salt obtainable according to the process is converted into the free compound of the formula I or into another salt, or a mixture of isomers obtainable according to the process is separated and the desired compound is isolated.

A radical $Z_1$ which can be convened into the variable —C(=NOH)—$NH_2$ is, for example, cyano, (lower) alkoxy-iminocarbonyl or halogeno-iminocarbonyl [halogeno-C(=NH)—].

Protected forms of hydroxylamine are those wherein the hydroxy group is protected for example as a benzyl ether or tetrahydropyranyl ether. Removal of said protecting groups is carried out according to methods well known in the art, e.g. hydrogenolysis or acid hydrolysis, respectively.

The reactions described herein are carried out in a manner known per se, for example in the absence or in the customary manner in the presence of a suitable solvent or diluent or a mixture thereof, the reaction being carried out, according to need, with cooling, at room temperature or with warming, for example in a temperature range from about —80° C. up to the boiling point of the reaction medium, preferably from about —10° C. to about +180° C., and, if necessary, in a closed vessel, under pressure, in an inert gas atmosphere and/or under anhydrous conditions. Conditions are illustrated herein, including the examples.

In starting compounds and intermediates which are convened to the compounds of the invention in a manner described herein, functional groups present, such as carboxy and hydroxy groups, are optionally protected by conventional protecting groups that are common in preparative organic chemistry. Protected carboxy and hydroxy groups are those that can be converted under mild conditions into free carboxy and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, N.Y., 1973, T. W. Greene, "Protective Groups in Organic Synthesis", Wiley, N.Y., 1991.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

Also, a reactive esterified derivative of an alcohol in any of the reactions cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzenesulfonic acid or 4-bromobenzenesulfonic acid. A said reactive esterified derivative is especially halo, for example chloro, bromo or iodo, or aliphatically or aromatically substituted sulfonyloxy, for example methanesulfonyloxy, 4-methylbenzenesulfonyloxy (tosyloxy) or trifluoromethylsulfonyloxy.

In the above process, alkoxy-iminocarbonyl is, for example $C_1$–$C_4$-alkoxy-iminocarbonyl such as methoxy- or ethoxy-iminocarbonyl, whereas halogeno-iminocarbonyl is, for example chloro-iminocarbonyl.

Preferably, those compounds of the formula II are employed in which $Z_2$ is cyano or $C_1$–$C_4$-alkoxy-iminocarbonyl such as methoxy- or ethoxy-iminocarbonyl. The reaction is preferably carried out by reacting with a hydroxylamine salt in the presence of a base such as sodium hydroxide, sodium ethoxide, lithium hydroxide and the like in a polar solvent such as ethanol at elevated temperature, e.g. up to reflux temperature.

The starting materials of formula II wherein $Z_1$ is cyano can be prepared for example (a) by reacting, a compound of formula III

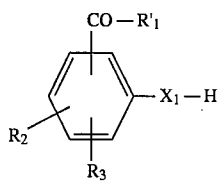

wherein $R'_1$ is $R_1$ as defined above but may also represent hydroxy or lower alkoxy and $X_1$, $R_2$ and $R_3$ have meaning as defined above, in the presence of a base, with a compound of the formula IV

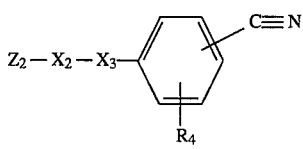

wherein $Z_2$ is a reactive esterified hydroxy leaving group, and $X_2$, $X_3$ and $R_4$ have meaning as defined above; or
(b) by reacting a compound of formula V

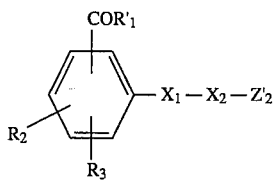

wherein $R'_1$, $R_2$, $R_3$, $X_1$ and $X_2$ have meaning as defined above, and $Z'_2$ represents a reactive esterified hydroxy leaving group, in the presence of a base, with a compound of formula VI

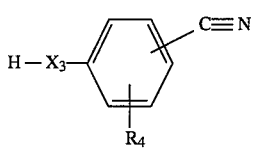

wherein $R_4$ and $X_3$ have meaning as defined hereinabove.

Reactive esterified hydroxy (e.g. for $Z_2$ or $Z'_2$) is preferably halo, e.g. bromo or iodo, or methanesulfonyloxy.

The reaction is preferably carried out as mentioned above in the presence of a base, such as potassium carbonate in an inert solvent such as acetonitrile or sodium hydride in a polar inert solvent such as dimethylformamide.

The starting materials of formula IV and V can in turn be prepared e.g. by reacting, in the presence of a base, a compound of formula VI and III, respectively, with a compound of formula VII $$Z_3\text{—}X_2\text{—}Z'_3 \qquad (VII)$$

wherein $X_2$ has meaning as defined hereinabove and both $Z_3$ and $Z'_3$ represent reactive esterified hydroxy or a functional group convertible thereto (preferably halogen); advantageously $Z_3$ and $Z'_3$ are not identical, e.g. one represents bromo while the other represents chloro.

The starting materials of formula III, VI and VII are either known or can be prepared according to methods well known in the art. In any of the above intermediates, $COR'_1$ being carboxyl or esterified carboxyl can be convened into any of the other meanings for $COR_1$ in any appropriate intermediate according to methods well-known in the art. For example, the acid can first be convened to an anhydride, acid halide or mixed anhydride and then reacted with the amine corresponding to $R_1$, preferably in the presence of a base such as pyridine, triethylamine or potassium carbonate in an inert solvent such as dichloromethane. Alternately, the acid can be condensed with the amine in the presence of a condensing agent such as N,N'-dicyclohexylcarbodiimide.

The nitriles of formula II (or any nitrile intermediates) can be convened to iminoethers, the compounds of formula II wherein $Z_1$ is ethoxyiminocarbonyl, by treatment with ethanol and anhydrous hydrogen chloride. The iminoethers can then be convened to compounds of the invention by treatment with hydroxylamine or a derivative thereof.

Relating to compounds wherein $R_2$ represents lower alkoxy substituted by carboxy, by esterified carboxy or by amidated carboxy, such compounds can be prepared from intermediates obtained by alkylation of starting materials or intermediates wherein $R_2$ is hydroxy with the appropriate reactive esterified hydroxy-substituted carboxylic acids or amides, e.g. the bromo-substituted lower alkyl carboxylic acid esters or amides. The esters can in turn be convened to the carboxylic acids or amides by methods well-known in the art. The starting materials and intermediates wherein $R_2$ is hydroxy are prepared from compounds wherein $R_2$ is e.g. methoxy by solvolysis thereof, e.g. with boron tribromide.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

A compound according to the invention which is obtainable by the process can be convened into another compound according to the invention in a manner known per se.

If one of the variables contains mono-substituted amino (for example $R_1$), corresponding compounds of the formula I or salts thereof can be N-alkylated in a manner known per se; likewise, N-mono-substituted carbamoyl (for example $R_1$) can be further N-alkylated or (aryl-)alkylated. The reaction is carried out, for example, using a reactive ester of an (aryl-)$C_1$–$C_7$-alkyl halide, for example a bromide or iodide, an (aryl-)$C_1$–$C_7$-alkylsulfonate, for example a methanesulfonate or p-toluenesulfonate, or using a di-$C_1$–$C_7$-alkyl sulfate, for example dimethyl sulfate, preferably under basic conditions, such as in the presence of sodium hydroxide solution or potassium hydroxide solution, and advantageously in the presence of a phase-transfer catalyst, such as tetrabutylammonium bromide or benzyltrimethylammonium chloride, where, however, stronger basic condensing agents, such as alkali metal amides, hydrides or alkoxides, for example sodium amide, sodium hydride or sodium ethoxide, may be necessary.

If the compounds of the invention contain unsaturated radicals, such as (lower)alkenyl groups, these can be convened into saturated radicals in a manner known per se. Thus, for example, multiple bonds are hydrogenareal by catalytic hydrogenation in the presence of hydrogenation catalysts, suitable for this purpose being, for example, nickel, such as Raney nickel, and noble metals or their derivatives, for example oxides, such as palladium or platinum oxide, which may be applied, if desired, to support materials, for example to carbon or calcium carbonate.

The invention also relates to any novel starting materials and processes for their manufacture and their use.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. Finally, the compounds of the invention are either obtained in the free form. or as a salt thereof.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal, topical, ocular and parenteral administration to mammals, including man, to antagonize $LTB_4$ receptors, and for the treatment of a condition or syndrome responsive to the selective antagonism of $LTB_4$ receptors, comprising an effective amount of a pharmacologically active compound of the invention, alone or in combination, with one or more pharmaceutically acceptable carriers.

The novel pharmaceutical products contain, for example, from about 10% to about 80 %, preferably from about 20% to about 60%, of the active compound. Examples of pharmaceutical products according to the invention for enteral or parenteral administration are those in dose-unit forms such as coated tablets, tablets, capsules or suppositories, as well as ampoules. These are prepared in a manner known per se, for example using conventional mixing, granulating, coating, dissolving or freeze-drying processes. Thus, pharmaceutical products for oral use can be obtained by combining the active compound with solid excipients, where appropriate granulating a mixture which is obtained, and processing the mixture or granules, if desired or necessary, after addition of suitable auxiliaries to tablets or cores of coated tablets.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. Cores of coated tablets are provided with suitable, optionally enteric, coatings, using, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose products such as acetyl cellulose phthalate or hydroxypropylmethylcellulose phthalate. Colorants or pigments can be added to the tablets or coatings of coated tablets, for example, to identify or to indicate various doses of active compound. In addition, they may also contain other therapeutically valuable substances. Said compositions are prepared according to conventional mixing, granulating or coating methods, respectively, and contain about 0.1 to 75 %, preferably about 1 to 50 %, of the active ingredient.

Suitable formulations for topical application, e.g. to the skin and eyes, are preferably aqueous solutions, ointments, creams or gels well-known in the art.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

In conjunction with another active ingredient, a compound of the invention may be administered either simultaneously, before or after the other active ingredient, either separately by the same or different mute of administration or together in the same pharmaceutical formulation.

The invention further particularly relates to a method for the treatment of a condition or syndrome responsive to the selective antagonism of $LTB_4$ receptors, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma; also for the treatment of osteoarthritis, of pain and of ocular allergies and inflammations; and also for the treatment of atopic and contact dermatitis.

The dosage of active compound administered is dependent on the species of warm-blooded animal (mammal), the body weight, age and individual condition, and on the form of administration. A unit dosage for oral administration to a mammal of about 70 kg may contain e.g. between about 1 and about 100 mg/kg per day of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1

A stirred solution of 2-acetoxy-4-[5-(4-cyanophenoxy)pentyloxy]-N,N-bis(1-methylethyl)benzamide (20 g, 42.9 mmol) in 20 mL of water and 350 mL of ethanol is treated with sodium hydroxide (3.43 g, 85.8 mmol) and hydroxylamine hydrochloride (5.97 g, 85.9 mmol). After refluxing overnight, the reaction is concentrated in vacuo. The resulting material is purified by chromatography on silica gel (500 g) with 65–100% ethyl acetate/hexane followed by 30% methanol/ethyl acetate as the eluent. After concentration in vacuo, the residue is recrystallized with methanol, ethyl acetate, and hexane to afford 4-[5-[4-[amino(hydroxyimino)methyl]phenoxy]pentyloxy]-2-hydroxy-N,N-bis(1-methylethyl)benzamide as colorless crystals, mp=195°–197° C.;

CHN for $C_{25}H_{35}N_3O_5$: Theory: % C: 65.62; % H: 7.71; % N: 9.18; Found: % C: 65.68; % H: 7.84; % N: 8.90.

The starting material, 2-acetoxy-4-[5-(4-cyanophenoxy)pentyloxy]-N,N-bis(1-methylethyl)benzamide, can be prepared, for example, as follows:

A stirred solution of 4-cyanophenol (80.9 g, 0.679 mol) in 1260 mL of acetonitile is treated with potassium carbonate (93.9 g, 0.679 tool) and 1-bromo-5-chloropentane (126 g, 0.679 mmol). The reaction is refluxed overnight and potassium carbonate is filtered off. The filtrate is concentrated in vacuo to generate oil which is partitioned between ether and water. The organic layer is washed with water, dried with magnesium sulfate, and concentrated in vacuo to afford 5-(4-cyanophenoxy)pentyl chloride as a white solid.

A stirred solution of 2,4-dihydroxy-benzoic acid (10 g, 64.9 mmol) in 200 mL of N,N-dimethylformamide is treated with 60% sodium hydride (7.8 g, 195 mmol). After stirring at 0° C. for 10 minutes, the reaction is treated with 5-(4-cyanophenoxy)pentyl chloride (14.5 g, 64.9 mmol) and stiffed at 70° C. overnight. The reaction is partitioned between ethyl acetate and 1N hydrochloride solution. The organic layer is washed with 1N hydrochloric acid and brine, dried over sodium sulfate, and concentrated in vacuo to 100 mL. The resulting material is treated with hexane and the precipitate is filtered to generate 4-[5-(4-cyanophenoxy)pentyloxy]-2-hydroxy-benzoic acid as a colorless solid.

A stirred solution of 4-[5-(4-cyanophenoxy)pentyloxy]-2-hydroxy-benzoic acid (28 g, 82 mmol) in 300 mL of dichloromethane is treated with pyridine (13.3 mL, 164 mmol) and acetic anhydride (9.3 mL, 98.4 retool) and stirred at room temperature for 30 minutes. The reaction is concentrated in vacuo and the residue is partitioned between ethyl acetate and 1N hydrochloric acid. The organic phase is washed with 1N hydrochloric acid and brine, dried over sodium sulfate, and concentrated in vacuo. The resulting 2-acetoxy-4-[5-(4-cyanophenoxy)pentyloxy]-benzoic acid is then dissolved in 300 mL of dichloromethane and treated at 0° C. with oxalyl chloride (8.6 mL, 98.4 mmol) and N,N-dimethylformamide (7.6 mL, 98.4 mmol). This solution is stirred at room temperature for 30 minutes and treated with 30 mL of diisopropylamine at 0° C. After stirring at room temperature for 30 minutes, the reaction is filtered and the filtrate is concentrated in vacuo. The resulting material is partitioned between ethyl acetate and 1N hydrochloric acid. The organic phase is washed with brine, dried over sodium sulfate, and concentrated in vacuo to afford 2-acetoxy-4-[5-(4-cyanophenoxy)pentyloxy]-N,N-bis(1-methylethyl)benzamide.

EXAMPLE 2

In a way analogously as described in Example 1, the following compound can be prepared.

4-[5-[4-[amino(hydroxyimino)methyl]phenoxy]pentyloxyl-2-hydroxy-N -(1-methylethyl)-N-phenylbenzamide is obtained from 2-acetoxy-4-[5-(4-cyanophenoxy)pentyloxy]-N-(1-methylethyl)-N-phenylbenzamide as white crystals, m.p.=133°–135° C.;

CHN for $C_{28}H_{33}N_3O_5$: Theory: % C: 68.41; % H: 6.77; % N: 8.55; Found: % C: 68.10; % H: 6.91; % N: 8.35.

EXAMPLE 3

A stirred solution of ethyl 5-[5-(4-cyanophenoxy)pentyloxy]-2-[N,N-bis(1-methylethyl)aminocarbonyl] phenoxyacetate (970 mg, 1.9 mmol) in 20 mL of anhydrous ethanol is treated with hydroxylamine hydrochloride (400 mg, 5.7 mmol) and 21% sodium ethoxide solution in ethanol (2.1 mL, 5.7 mmol) and stirred at 50° C. overnight. The reaction is concentrated in vacuo and purified by chromatography on silica gel (20 g) with 80–100% ethyl acetate/hexane followed by 0–10% methanol/ethyl acetate as the eluent to afford (a) ethyl 2-[5-[5-[4-[amino(hydroxyimino)methyl]phenoxy]pentyloxy]-2-[N,N-bis( 1 -methylethyl)carbamoyl]phenoxy]acetate as a colorless foam;

CHN calculated for $C_{29}H_{41}N_3O_7$: Theory: % C: 64.07; % H: 7.60; % N: 7.33; Found: % C: 64.43; % H: 7.51% N: 7.58; and (b) 4-[5-[4-[amino(hydroxyimino)methyl]phenoxy]pentyloxy]-2-[(N-hydroxycarbamoyl)methoxy] -N,N-bis(1-methylethyl)benzamide as a colorless foam;

CHN calculated for $C_{27}H_{38}N_4O_7$: Theory: % C: 61.12; % H: 7.22; % N: 10.56; Found: % C: 61.37; % H: 7.22; % N: 10.29.

The starting material, ethyl 5-[5-(4-cyanophenoxy)pentyloxy]-2-[N,N-bis(1-methylethyl)aminocarbonyl] phenoxyacetate, can be prepared, for example, as follows:

A stirred solution of 4-[5-(4-cyanophenoxy)pentyloxy]-2-hydroxy-N,N-bis(1-methylethyl)benzamide (1.0 g, 2.36 mmol) in 10.0 mL of N,N-dimethylformamide is treated with 60% sodium hydride (100 mg, 2.59 mmol) and ethyl bromoacetate (290 µL, 2.59 mmol), and the mixture is heated at 70° C. overnight; the reaction is partitioned between ethyl acetate and water, dried over sodium sulfate and concentrated in vacuo to afford a yellow foam. This material is purified by chromatography on silica gel (30 g) with 40–50% ethyl acetate/hexane as the eluent to afford ethyl 5-[5-(4-cyanophenoxy )pentyloxy]-2-[N,N-bis(1-methylethyl)aminocarbonyl]phenoxyacetate as a colorless foam.

EXAMPLE 4

A stirred solution of ethyl 2-[5-[5-(4-cyanophenoxy)pentyloxy]-2-[N,N-bis(1 -methylethyl)aminocarbonyl]phenoxy]-2-methylpropanoate (1.2 g, 2.3 mmol) in 30 mL of anhydrous ethanol is treated with hydroxylamine hydrochloride (480 mg, 6.8 mmol) and 21% sodium ethoxide solution in ethanol (2.6 mL, 6.8 mmol) and stirred at 50° C. overnight. The reaction is concentrated in vacuo and purified by chromatography on silica gel (20 g) with 80% ethyl acetate/ hexane as the eluent to afford ethyl 2-[5-[5-[4-[amino(hydroxyimino)methyl]-phenoxy] pentyloxy]-2-[N,N-bis( 1-methylethyl)carbamoyl]phenoxy]-2-methylpropanoate as a colorless foam;

CHN for $C_{31}H_{45}N_3O_7$-1.0 $H_2O$: Theory: % C: 63.14; % H: 8.03; % N: 7.13; Found: % C: 62.99; % H: 7.84; % N: 7.06.

The starting material, ethyl 2-[5-[5-(4-cyanophenoxy)pentyloxy]-2-[N,N-bis(1-methylethyl) aminocarbonyl]phenoxy]-2-methylpropanoate, can be prepared, for example, as follows:

A stirred solution of 2-acetoxy-4-[5-(4-cyanophenoxy)pentyloxy]-N,N-bis(1-methylethyl)benzamide (10 g, 21.5 mmol) in 250 mL of ethanol is treated with 1N sodium hydroxide solution (25 mL, 25 mmol). After stirring at room temperature for 2 hours, the reaction is concentrated in vacuo. This material is partitioned between ethyl acetate and 1N hydrochloric acid. The organic phase is washed with brine, dried over sodium sulfate, and concentrated in vacuo. The resulting material is purified by chromatography on silica gel (200 g) with 40–50% ethyl acetate/hexane as the eluent to afford 4-[5-(4-cyanophenoxy)pentyloxy] -2-hydroxy-N,N-bis(1-methylethyl)benzamide as a colorless foam.

A stirred solution of 4-[5-(4-cyanophenoxy)pentyloxy]-2-hydroxy-N,N-bis(1-methylethyl)benzamide (5.7 g, 13.4 mmol) in 50 mL of acetone is treated with sodium hydroxide (5.4 g, 134 mmol) and heated to reflux. The reaction is treated slowly with chloroform (1.4 mL, 17.4 mmol) in 150 mL of acetone and refluxed for 4 hours. The reaction is concentrated in vacuo and the residue is partitioned between ethyl acetate and 1N hydrochloric acid. The organic phase is washed with brine, dried over magnesium sulfate, and concentrated in vacuo. The resulting material is purified by chromatography on silica gel (200 g) with 0–10% methanol/ ethyl acetate as the eluent to afford 2-[5-[5-(4-cyanophenoxy)pentyloxy]-2-[N,N -bis(1-methylethyl)aminocarbonyl]phenoxy]-2-methylpropanoic acid as a colorless foam.

A stirred solution of 2-[5-[5-(4-cyanophenoxy)pentyloxy] -2-[N,N-bis(1 -methylethyl)aminocarbonyl]phenoxy]-2-methylpropanoic acid (2.0 g, 4.0 mmol) in 50 mL of dichloromethane is treated with 1-ethyl-3-[3-(dimethylamino)propyl]-carbodiimide hydrochloride (770 mg, 4.0 mmol), hydroxybenztriazole (540 mg, 4.0 mmol), and ethanol (220 mg, 4.8 mmol) and stirred at room temperature over 3 days. The reaction is concentrated in vacuo and purified by chromatography on silica gel (60 g) with 40–50% ethyl acetate/hexane as the eluent to afford ethyl 2-[5-[5-(4-cyanophenoxy)pentyloxy]-2 -[N,N-bis(1-methylethyl)aminocarbonyl]phenoxy]-2- methylpropanoate as a colorless foam.

EXAMPLE 5

A stirred solution of 2-[5-[5-(4-cyanophenoxy)pentyloxy] -2-[N,N-bis(1 -methylethyl)aminocarbonyl]phenoxy]-2-methylpropionic acid (1.4 g, 2.8 mmol) in 30 mL of anhydrous ethanol is treated with hydroxylamine hydrochloride (590 mg, 8.4 mmol) and 21% sodium ethoxide solution in ethanol (3.1 mL, 5.7 mmol) and stirred at 50° C. overnight. The reaction is concentrated in vacuo and purified by chromatography on silica gel (20 g) with 80–100% ethyl acetate/ hexane followed by 0–10% methanol/ethyl acetate as the eluent to afford 2-[5-[5-[4-[amino(hydroxyimino)methyl]phenoxy]pentyloxy]2-[N,N-bis(1-methylethyl) -aminocarbonyl]phenoxy]-2-methylpropanoic acid sodium salt as a colorless foam;

CHN for $C_{29}H_{40}N_3O_7Na$-1.5 $H_2O$); Theory: % C: 58.77; % H: 7.31; % N: 7.09; Found: % C: 58.62; % H: 7.03; % N: 6.79.

EXAMPLE 6

A stirred solution of 4-[5-(4-cyanophenoxy)-pentyloxy]-N,N-bis(1-methylethyl)benzamide (300 mg, 0.73 mmol) in 2 mL of water and 8 mL of ethanol is treated with sodium hydroxide (32 mg, 0.81 mmol) and hydroxylamine hydrochloride (56 mg, 0.81 mmol). After refluxing overnight, the reaction is partitioned between dichloromethane and brine. The organic phase is dried over sodium sulfate, and concentrated in vacuo. The resulting material is purified by chromatography on silica gel (10 g) with 70–80% ethyl acetate/hexane as the eluent to afford 4-[5-[4-[amino(hydroxyimino)methyl]phenoxy]pentyloxy]-N,N-bis -(1-methylethyl)benzamide as colorless crystals, m.p.=146°–149° C.;

CHN for $C_{25}H_{35}N_3O_4$: Theory: % C: 68.00; % H: 7.99; % N: 9.52; Found: % CL 68.29; % H: 8.19; % N: 9.41.

The starting material, 4-[5-(4-cyanophenoxy)pentyloxy]-

N,N-bis(1-methylethyl)benzamide, can be prepared, for example, as follows:

A stirred solution of 4-hydroxybenzoic acid (5 g, 36.2 mmol) in 50 mL of dichloromethane is treated at 0° C. with oxalyl chloride (6.3 mL, 72.4 mmol) and N,N-dimethylformamide (5.6 mL, 72.4 mmol). This solution is stirred at room temperature for 2 hours and treated with diisopropylamine (40 mL, 286 mmol) at 0° C. After stirring at room temperature for overnight, the reaction is partitioned between ethyl acetate and 1N hydrochloride solution. The organic phase is washed with brine, dried over sodium sulfate, and concentrated in vacuo to afford 4-hydroxy-N, N-bis(1-methylethyl)benzamide.

A stirred solution of 4-hydroxy-N,N-bis(1-methylethyl)benzamide (2.47 g, 11.2 mmol) in 50 mL of N,N-dimethylformamide is treated with 60% sodium hydride (500 mg, 12.5 mmol). After stirring at 0° C. for 10 minutes, the reaction is treated with 5-(4-cyanophenoxy)pentyl chloride (3.25 g, 14.5 mmol) and stirred at 70° C. for 2 hours. The reaction is partitioned between ethyl acetate and water. The organic layer is washed with water and brine, dried over sodium sulfate, and concentrated in vacuo. The resulting material is purified by chromatography on silica gel (60 g) with 70–80% ethyl acetate/hexane as the eluent to afford 4-[5-(4-cyanophenoxy)pentyloxy]N,N-bis(1-methylethyl)benzamide.

EXAMPLE 7

In a way analogously as described in example 6, the following compounds can be prepared:

(a) 4-[5-[4-[amino(hydroxyimino)methyl]phenoxy]pentyloxy]-N-(1-methylethyl) -N-phenylbenzamide is obtained from 4-[5-(4-cyanophenoxy)pentyloxy]-N-(1-methylethyl) -N-phenylbenzamide as crystals, mp=60°–62° C.;

CHN for $C_{28}H_{33}N_3O_4$: Theory: % C: 70.71; % H: 6.99; % N: 8.84; Found: % C: 70.40; % H: 6.87; % N: 8.56.

(b) 4-[5-[4-[amino(hydroxyimino)methyl]phenoxy]pentyloxy]-2-chloro-N-(1-methyl -ethyl)-N-phenylbenzamide is obtained from 4-[5-(4-cyanophenoxy)pentyloxy]-2-chloro-N -(1-methylethyl)-N-phenylbenzamide as crystals, mp=60°–63° C.

EXAMPLE 8

A stirred solution of 4-[4-(4-cyanophenoxy)butoxy]-3-methoxy-N,N-bis(1-methylethyl)benzamide (500 mg, 1.18 mmol) in 2 mL of water and 8 mL of ethanol is treated with sodium hydroxide (57.7 mg, 1.34 mmol) and hydroxylamine hydrochloride (90 mg, 1.29 mmol). After refluxing overnight, the reaction is partitioned between dichloromethane and brine. The organic phase is dried over magnesium sulfate, and concentrated in vacuo. The resulting material is purified by chromatography on silica gel (15 g) with ethyl acetate as the eluent to afford 4- [4-[4-[amino(hydroxyimino)methyl]phenoxy]butoxy]-3-methoxy-N,N-bis(1 -methylethyl)benzamide as colorless crystals, mp=63°–65° C.;

CHN for $_{25}H_{35}N_3O_5$: Theory: % C: 65.62; % H: 7.71; % N: 9.18; Found: % C: 65.53; % H: 7.56; % N: 9.28.

The starting material, 4-[4-(4-cyanophenoxy)butoxy]-3-methoxy-N,N-bis(1-methylethyl)benzamide, can be prepared, for example, as follows:

A stirred solution of 4-hydroxy-3-methoxy-benzoic acid (5 g, 29.7 mmol) in 35 mL of dichloromethane is treated with thionyl chloride (20 mL, 377 mmol) and N,N-dimethylformamide (1.0 mL, 12.9 mmol). This solution is refluxed for 45 minutes and concentrated in vacuo. The resulting material is dissolved in 125 mL of dichloromethane and treated with diisopropylamine (20 mL, 143 mmol). After stirring at room temperature for 5 minutes, the reaction is diluted with ethyl acetate and filtered. The filtrate is washed with 1N hydrochloride solution, and brine, dried over magnesium sulfate, and concentrated in vacuo to afford 4-hydroxy-3-methoxy-N,N-bis(1-methylethyl)benzamide as a colorless solid.

A stirred solution of 4-hydroxy-3-methoxy-N,N-bis(1-methylethyl)benzamide (1.0 g, 4.0 mmol) in 50 mL of N,N-dimethylformamide is treated with 60% sodium hydride (160 mg, 4.0 mmol). After stirring at 0° C. for 10 minutes, the reaction is treated with 4-(4-cyanophenoxy)butyl chloride (835 mg, 4.0 mmol) and stirred at 60° C. for 4 days. The reaction is partitioned between diethyl ether and water. The organic layer is washed with brine, dried over magnesium sulfate, and concentrated in vacuo. The resulting material is purified by chromatography on silica gel (30 g) with 60 % ethyl acetate/hexane as the eluent to afford 4-[4-(4-cyanophenoxy)butoxy]-3-methoxy-N,N-bis(1-methylethyl)benzamide as an oil.

EXAMPLE 9

In a way analogously as described in example 8, the following compounds can be prepared:

(a) 4-[6-[4-[amino(hydroxyimino)methyl]phenoxy]hexyloxy]-3-methoxy-N,N-bis(1 -methylethyl)benzamide is obtained from 4-[6-(4-cyanophenoxy)hexyloxy]-3-methoxy -N,N-bis(1-methylethyl)benzamide as a colorless foam;

CHN for $C_{27}H_{39}N_3O_5$-0.5 $H_2O$: Theory: % C: 65.56; % H: 8.15; % N: 8.50; Found: % C: 65.90; % H: 8.37; % N: 8.01.

(b) 4-[5-[4-[amino(hydroxyimino)methyl]phenoxy]pentyloxy]-3-methoxy-N,N-bis (1-methylethyl)benzamide is obtained from 4-[5-(4-cyanophenoxy)pentyloxy] -3-methoxy-N,N-bis(1-methylethyl)benzamide as colorless crystals, m.p.=56°–58° C.;

CHN for $C_{26}H_{37}N_3O_5$-1.0 $H_2O$: Theory: % C: 63.78; % H: 8.03; % N: 8.58; Found: % C: 64.08; % H: 7.82; % N: 8.55.

The starting material, 4-[5-(4-cyanophenoxy)pentyloxy]-3-methoxy-N,N-bis (1-methylethyl)benzamide, can be prepared, for example, as follows:

A stirred solution of 1-bromo-5-chloropentane (50 g, 0.270 tool) in acetonitrile (500 mL) is treated with 4-cyanophenol (32.10 g, 0.270 mol) and powdered potassium carbonate (37.25 g, 0.270 mol). This suspension is refluxed with stirring under nitrogen for 5.5 hours. The reaction is cooled slightly and treated with additional powdered potassium carbonate (37.25 g, 0.270 mol), potassium iodide (44.75 g, 0.270 mol) and methyl vanillate (49.11 g, 0.270 mol). The reaction mixture is heated under nitrogen for 24 hours and treated with 4N sodium hydroxide solution (135 mL, 0.540 mol). After refluxing for 24 hours, the reaction mixture is again treated with 67.5 mL of 4N sodium hydroxide solution (0.270 mol). After refluxing overnight, the reaction mixture is treated with 67.5 mL of 4N sodium hydroxide solution (0.270 mol). After refluxing for 30 minutes, the reaction mixture is cooled to room temperature and again treated with 34 mL of 4N sodium hydroxide solution (0.135 mol). After refluxing for 5 hours, the reaction mixture is stirred through the weekend. The reaction is poured slowly into a solution of 1500 mL of water and 60 mL of acetic acid. The precipitate is filtered and washed with ice cold acetonitrile to afford 4-[5-(4-cyanophenoxy)pentyloxy] -3-methoxy-N,N-bis(1-methylethyl)benzoic acid as a white solid.

A stirred solution of 4-[5-(4-cyanophenoxy)pentyloxy]-3-methoxy-N,N-bis(1-methylethyl)benzoic acid (7.24 g, 20.4 mmol) in 65 mL of dichloromethane is treated at 0° C. with thionyl chloride (7.43 mL, 102 mmol) and N,N-dimethylformamide (7.2 mL, 93 mmol). This reaction mixture is refluxed overnight and concentrated in vacuo. The resulting material is dissolved with 100 mL of dichloromethane and treated with diisopropylamine (17 mL, 119 mmol). After stirring at room temperature for 4 hours, the reaction is concentrated in vacuo. The resulting material is partitioned between ethyl acetate and 1N hydrochloride solution. The organic phase is washed with brine, dried over magnesium sulfate, and concentrated in vacuo. The resulting material is purified by chromatography on silica gel (300 g) with 60 % ethyl acetate/hexane as the eluent to afford 4-[5-(4-cyanophenoxy)pentyloxy] -3-methoxy-N,N-bis(1-methylethyl)benzamide as a colorless solid.

EXAMPLE 10

A stirred solution of 4-[5-(4-cyano-3-fluoro-phenoxy)pentyloxy]-N,N-bis(1-methylethyl)benzamide (360 mg, 0.84 mmol) in 1.7 mL of 1N sodium hydroxide (1.7 mmol) and 10 mL of ethanol is treated with hydroxylamine hydrochloride (120 mg, 1.7 mmol). After refluxing overnight, the reaction is concentrated in vacuo. The resulting material is purified by chromatography on silica gel (500 g) with 60–70% ethyl acetate/hexane as the eluent to afford 4-[5-[4-[amino(hydroxyimino)methyl]-3-fluoro-phenoxy]pentyloxy]-N,N-bis (1-methylethyl)benzamide as a colorless foam;

CHN for $C_{25}H_{34}F_1N_3O_4$: Theory: % C: 65.34; % H: 7.46; % N: 9.14; Found: % C: 65.70; % H: 7.73; % N: 8.86.

The starting material, 4-[5-(4-cyano-3-fluoro-phenoxy)pentyloxy]-N,N-bis(1-methylethyl)benzamide, can be prepared, for example, as follows:

A stirred solution of 3-fluoroanisole (7.0 g, 50.3 mmol) in 50 mL of chloroform is treated with bromine (2.59 mL, 50.3 mmol) over 30 minutes at room temperature. The reaction is heated to 60° C. for 7 hours and concentrated in vacuo. The resulting material is dissolved in 10 mL of N,N-dimethylformamide and treated with copper cyanide (5.9 g, 65.39 mmol). After refluxing overnight, the reaction is partitioned between ethyl acetate and acidic ferric chloride solution (a mixture of 19.2 g of ferric chloride hexahydrate, 44.8 mL of hydrochloric acid, and 48 mL of water). The organic phase is washed with brine, dried over magnesium sulfate, and concentrated in vacuo. The resulting material is purified by chromatography on silica gel (210 g) with 10% ethyl acetate/hexane as the eluent to afford 2-fluoro-4-methoxy-benzonitrile.

A mixture of 2-fluoro-4-methoxy-benzonitrile (500 mg, 0.246 mmol) and pyridine hydrochloride (2.0 g, 17.2 mmol) is heated at 170° C. for 5 hours. The reaction is partitioned between ethyl acetate and 1N hydrochloric acid. The organic phase is washed with brine, dried over sodium sulfate, and concentrated in vacuo to afford 2-fluoro-4-hydroxy-benzonitrile.

A stirred solution of 4-hydroxy-N,N-bis(1-methylethyl)benzamide (500 mg, 2.3 mmol) in 5 mL of N,N-dimethylformamide is treated with 1-bromo-5-chloropentane (300 μL, 2.3 mmol) and cesium carbonate (750 mg, 2.3 mmol) and heated for 2 hours. This is treated with a mixture of 2-fluoro-4-hydroxy-benzonitrile, and 60% sodium hydride (92 mg, 2.3 mmol) in 2 mL of N,N-dimethylformaide followed by sodium iodide (1.04 g, 6.9 mmol). The reaction is heated to 70° C. for 6 hours and partitioned between ethyl acetate and water. The organic phase is washed with brine, dried over sodium sulfate, and concentrated in vacuo. The resulting material is purified by chromatography on silica gel (20 g) with 70% ethyl acetate/hexane as the eluent to afford 4-[5-(4-cyano-3-fluoro-phenoxy)pentyloxy]-N,N-bis(1-methylethyl)benzamide.

EXAMPLE 11

A stirred solution of 4-[5-[4-[amino(hydroxyimino)methyl]phenoxy]pentyloxy] -3-methoxy-N,N-bis(1-methylethyl)benzamide (200 mg, 0.4 mmol) in 4 mL of dichloromethane at 0° C. is treated with aluminum chloride (292 mg, 2.2 mmol) and ethanethiol (4 mL, 54 mmol). After stirring at 0° C. for 1 hour, reaction mixture is partitioned between ethyl acetate and saturated ammonium hydroxide solution. The organic phase is dried with magnesium sulfate and concentrated in vacuo. The resulting material is purified by chromatography on silica gel (10 g) with 5% methanol/dichloromethane as the eluent to afford 4-[5-[4-[amino(hydroxyimino)methyl]phenoxy]pentyloxy]-3-hydroxy-N,N-bis(1 -methylethyl)benzamide as a colorless foam;

CHN for $C_{25}H_{35}N_3O_5$: Theory: % C: 65.62; % H: 7.71; % N: 9.18; Found: % C: 65.46; % H: 7.49; % N: 8.97.

EXAMPLE 12

Preparation of 3000 capsules each containing 10 mg of the active ingredient, for example, 4-[5-[4-[amino(hydroxyimino)methyl]phenoxy]pentyloxy]-2-hydroxy-N,N-bis-

| (1-methylethyl)benzamide | |
|---|---|
| Active ingredient | 30.00 g |
| Lactose | 800.00 g |
| Avicel PH 102 (microcrystalline cellulose) | 300.00 g |
| Polyplasdone XL (polyvinylpyrrolidone) | 30.00 g |
| Purified water | q.s |
| Magnesium stearate | 9.0 g |

The active ingredient is passed through a No. 30 hand screen.

The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and mixture is blended for 5 minutes in a mixer. The blend is encapsulated in No. 0 hard gelatin capsules each containing an amount of the blend equivalent to 25 mg of the active ingredient.

What is claimed is:

1. A compound of the formula

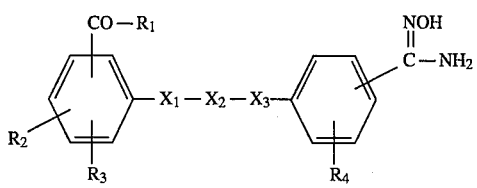

wherein the C(=NOH)-NH$_2$ group may be in tautomeric form and in which

R$_1$ is amino or amino which is mono- or disubstituted by a substituent selected from an aliphatic hydrocarbon radical, an araliphatic hydrocarbon radical, an aromatic radical, and a cycloaliphatic hydrocarbon radical or is amino which is disubstituted by a divalent aliphatic hydrocarbon radical or a said radical interrupted by oxygen;

R$_2$ is hydrogen, halogen, trifluoromethyl, an aliphatic hydrocarbon radical or hydroxy; or R$_2$ is hydroxy which is etherified by an aliphatic alcohol, araliphatic alcohol or aromatic alcohol, or which is esterified by an aliphatic or araliphatic carboxylic acid; or R$_2$ is hydroxy which is etherified by an aliphatic alcohol which is substituted by carboxy, by esterified carboxy or by amidated carboxy;

X$_1$ and X$_3$, are oxygen (—O—); and

X$_2$ is lower alkylene; and

R$_3$ and R$_4$, independently of one another, are hydrogen, halogen, trifluoromethyl, an aliphatic hydrocarbon radical, hydroxy or hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid; and wherein a cycloaliphatic hydrocarbon radical may be substituted by an aliphatic radical; or a pharmaceutically acceptable salt thereof.

2. A compound according to claim 1 in which R$_1$ is amino or amino which is mono- or disubstituted by a substituent selected from lower alkyl, lower alkenyl, lower alkynyl, phenyl-lower alkyl, phenyl-lower alkenyl, phenyl-lower alkynyl, phenyl, naphthyl, indanyl, fluorenyl, cycloalkyl, and cycloalkenyl, cycloalkyl and cycloalkenyl each being unsubstituted or mono- or polysubstituted by lower alkyl, or is amino which is disubstituted by lower alkylene;

R$_2$ is hydrogen, halogen, trifluoromethyl, lower alkyl, lower alkenyl, lower alkynyl, hydroxy, lower alkoxy, lower alkenyloxy, phenyl-lower alkoxy, phenoxy, lower alkanoyloxy, lower alkenoyloxy or phenyl-lower alkanoyloxy; or R$_2$ is lower alkoxy substituted by carboxy, lower alkoxycarbonyl, aminocarbonyl or mono- or di-lower alkylaminocarbonyl;

X$_1$ and X$_3$, are O;

X$_2$ is lower alkylene; and

R$_3$ and R$_4$ are, independently of one another, hydrogen, halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy or phenyl-lower alkanoyloxy;

wherein the aromatic radicals in the above definitions may be independently of one another, substituted by one or more substituents selected from halogen, trifluoromethyl, lower alkyl lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy; or a pharmaceutically acceptable salt thereof.

3. A compound according to claim 1 in which —CO—R$_1$ is located in position 4 (para) or 3 or 5 (meta) of the corresponding phenyl ring with respect to —X$_1$—; R$_2$— is located in position 2 (ortho) or 3 (meta) of the corresponding phenyl ring with respect to —X$_1$—; and —C(=NOH)—NH$_2$ is located in position 4 (para) of the corresponding phenyl ring with respect to —X$_3$—; or a pharmaceutically acceptable salt thereof.

4. A compound according to claim 1 of the formula IA

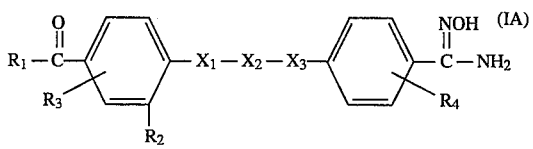

wherein the C(=NOH)—NH$_2$ group may be in tautomeric form, and in which R$_1$ is di-C$_1$–C$_4$-alkylamino, C$_1$–C$_4$alkyl-phenylamino, C$_1$–C$_4$alkyl-(phenyl-C$_1$–C$_4$-alkyl)-amino, di-C$_3$–C$_6$-cycloalkylamino which is unsubstituted or substituted by C$_1$–C$_4$-alkyl, or 1-piperidino which is unsubstituted or substituted by C$_1$–C$_4$-alkyl;

R$_2$ is hydrogen, hydroxy, halogen or C$_1$–C$_4$-alkoxy; or R$_2$ is C$_1$–C$_4$-alkoxy which is substituted by carboxy, lower alkoxycarbonyl, aminocarbonyl, hydroxyaminocarbonyl, or by mono- or di-lower alkylaminocarbonyl;

X$_1$ and X$_3$ are —O—;

X$_2$ is C$_4$–C$_7$-alkylene; and

R$_3$ and R$_4$ are hydrogen, halogen, trifluoromethyl, C$_1$–C$_4$-alkyl, or C$_1$–C$_4$-alkoxy; or a pharmaceutically acceptable salt thereof.

5. A compound according to claim 4 in which

R$_1$ is di-C$_1$–C$_4$-alkylamino or c$_1$–C$_4$alkyl-(phenyl)amino;

R$_2$ is hydrogen or C$_1$–C$_4$-alkoxy;

X$_1$ and X$_3$ are —O—;

X$_2$ is C$_4$–C$_7$-alkylene; and

R$_3$ and R$_4$ are hydrogen.

6. A compound according to claim 4 in which

R$_1$ is di-ethylamino, di-isopropylamino or phenyl-isopropyl-amino;

R$_2$ is hydrogen or methoxy;

X$_1$ and X$_3$ are —O—;

X$_2$ is pentylene; and

R$_3$ and R$_4$ are hydrogen.

7. A compound according to claim I of the formula IB

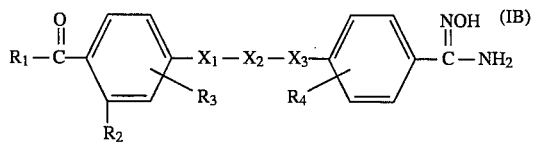

wherein the C(=NOH)—NH$_2$ group may be in tautomeric form, and in which

R$_1$ is di-C$_1$–C$_4$-alkylamino, C$_1$–C$_4$alkyl-(phenyl)amino, C$_1$–C$_4$-alkyl-(phenyl-C$_1$–C$_4$-alkyl)-amino, di-C$_3$–C$_6$-cycloalkylamino which is unsubstituted or substituted by C$_1$–C$_4$-alkyl, or 1-piperidino which is unsubstituted or substituted by C$_1$–C$_4$-alkyl, $R_2$ is hydrogen, hydroxy, halogen or $C_1$–$C_4$-alkoxy; or $R_2$ is $C_1$–$C_4$-alkoxy which is substituted by carboxy, lower alkoxycarbonyl, aminocarbonyl, hydroxyaminocarbonyl or by mono- or di-lower alkylaminocarbonyl;

$X_1$ and $X_3$ are —O—;

$X_2$ is $C_4$–$C_7$-alkylene; and $R_3$ and $R_4$ are independently of one another, hydrogen, halogen, trifluoromethyl, $C_1$–$C_4$-alkyl, or $C_1$–$C_4$-alkoxy; or a pharmaceutically acceptable salt thereof.

8. A compound according to claim 7 in which $R_1$ is di-$C_1$–$C_4$alkylamino or $C_1$–$C_4$-alkyl(phenyl)amino;

$R_2$ is hydrogen, fluoro, chloro, hydroxy or $C_1$–$C_4$-alkoxy; or $R_2$ is carboxy-$C_1$–$C_4$-alkoxy, $C_1$–$C_4$-alkoxycarbony-$C_1$–$C_4$-alkoxy, or carbamoyl-$C_1$–$C_4$-alkoxy;

$X_1$ and $X_3$ are —O—;

$X_2$ is $C_4$–$C_7$-alkylene; and $R_3$ and $R_4$ are hydrogen.

9. A compound according to claim 7 in which $R_1$ is di-ethylamino, di-isopropylamino or phenyl-isopropylamino;

$R_2$ is hydrogen, fluoro, chloro, methoxy or hydroxy; or $R_2$ is (carboxy, $C_1$–$C_4$-alkoxycarbonyl or carbamoyl)-substituted-$C_1$–$C_4$-alkoxy in which the oxygen and the substituent are separated by one carbon atom;

$X_1$ and $X_3$ are oxygen;

$X_2$ is pentylene; and $R_3$ and $R_4$ are hydrogen.

10. A compound according to claim 7 which is 4-[5-[4-[amino(hydroxyimino)methyl]-phenoxy] pentyloxy]-2-hydroxy-N,N-bis(1-methylethyl)benzamide, the compound of formula IB in which $R_1$ is di-isopropylamino; $R_2$ is hydroxy; $X_1$ and $X_3$ are O; $X_2$ is pentylene; and $R_3$ and $R_4$ are hydrogen.

11. A compound according to claim 7 which is 4-[5-[4-[amino(hydroxyimino)methyl]-phenoxy] pentyloxy]-2-hydroxy-N-(1-methylethyl)-N-phenylbenzamide, the compound of formula IB in which $R_1$ is phenyl-isopropyl-amino; $R_2$ is hydroxy; $X_1$ and $X_3$ are O; $X_2$ is pentylene; and $R_3$ and $R_4$ are hydrogen.

12. A compound according to claim 7 which is ethyl 2-[5-[5-[4-[amino(hydroxyimino)methyl] phenoxy]pentyloxy]-2-[N,N-bis(1-methyl-ethyl)carbamoyl]phenoxy]acetate, the compound of formula IB in which $R_1$ is di-isopropylamino; $R_2$ is ethoxycarbonylmethoxy; $X_1$ and $X_3$ are O; $X_2$ is pentylene; and $R_3$ and $R_4$ are hydrogen.

13. A compound according to claim 7 which is ethyl 2-[5-[5-[4-[amino(hydroxyimino)methyl] -phenoxy]pentyloxy]-2-[N,N-bis(1-methylethyl)carbamoyl]phenoxy]-2-methylpropanoate, the compound of formula IB in which $R_1$ is di-isopropylamino; $R_2$ is 2-ethoxycarbonyl-2-propyloxy; $X_1$ and $X_3$ are oxygen; $X_2$ is pentylene; and $R_3$ and $R_4$ are hydrogen.

14. A compound according to claim 7 which is 2-[5-[5-[4-[amino(hydroxyimino)-methyl] phenoxy]pentyloxy]-2-[N,N-bis(1-methylethyl)-aminocarbonyl]phenoxy]-2-methylpropanoic acid, the compound of formula IB in which $R_1$ is di-isopropylamino; $R_2$ is 2-carboxy-2-propyloxy; $X_1$ and $X_3$ are oxygen; $X_2$ is pentylene; and $R_3$ and $R_4$ are hydrogen.

15. A compound according to claim 7 which is 4-[5-[4-[amino(hydroxyimino)methyl]phenoxy] pentyloxy]-2-chloro-N-(1-methylethyl)-N-phenylbenzamide, the compound of formula IB in which $R_1$ is phenyl-isopropyl-amino; $R_2$ is chloro; $X_1$ and $X_3$ are 0; $X_2$ is pentylene; and $R_3$ and $R_4$ are hydrogen.

16. A pharmaceutical composition suitable for antagonizing $LTB_4$ for treating rheumatoid arthritis in mammals comprising an effective $LTB_4$ antagonizing amount of a compound of claim 1 and a pharmaceutically acceptable carrier.

17. A method of antagonizing $LTB_4$ for treating rheumatoid arthritis in mammals which comprises administering to a mammal in need thereof an effective $LTB_4$ antagonizing amount of a compound according to claim 1.

* * * * *